US012690871B2

(12) United States Patent
Tang

(10) Patent No.: US 12,690,871 B2
(45) Date of Patent: Jul. 28, 2026

(54) MEDICAL DEVICE FOR CAUSING HEMOSTASIS OF BLOOD VESSEL

(71) Applicant: MICRO-TECH (NANJING) CO., LTD., Nanjing (CN)

(72) Inventor: Zhi Tang, Nanjing (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 97 days.

(21) Appl. No.: 18/714,357

(22) PCT Filed: Feb. 25, 2022

(86) PCT No.: PCT/CN2022/078084
§ 371 (c)(1),
(2) Date: May 29, 2024

(87) PCT Pub. No.: WO2023/159518
PCT Pub. Date: Aug. 31, 2023

(65) Prior Publication Data
US 2025/0017596 A1    Jan. 16, 2025

(51) Int. Cl.
*A61B 17/122* (2006.01)
*A61B 17/128* (2006.01)
(Continued)

(52) U.S. Cl.
CPC ........ *A61B 17/122* (2013.01); *A61B 17/1285* (2013.01); *A61B 2017/00367* (2013.01); *A61B 2017/12004* (2013.01)

(58) Field of Classification Search
CPC .............. A61B 17/122; A61B 17/1285; A61B 17/1227; A61B 2017/00367;
(Continued)

(56) References Cited

U.S. PATENT DOCUMENTS

2005/0059985 A1* 3/2005 Kimura ................ A61B 17/083
606/151
2005/0070758 A1 3/2005 Wells et al.
(Continued)

FOREIGN PATENT DOCUMENTS

CN 110191684 A 8/2019
CN 111526803 A 8/2020
(Continued)

*Primary Examiner* — Brooke Labranche
(74) *Attorney, Agent, or Firm* — Bret E. Field; Bozicevic, Field & Francis LLP

(57) ABSTRACT
A medical device for causing the hemostasis of a blood vessel for use through an endoscope comprises: a handle; a sheath device; a clamp device including a clamp housing defining a longitudinal direction with a clamp base in particular in the form of a sleeve provided on the distal end of the sheath device and at least two, in particular exactly two clamp arms, said clamp housing defining an interior space; a control wire extending through the sheath device and reversibly movable in the distal and proximal direction; and an actuator coupled to the proximal end of the control wire and actuable to reversibly move the control wire in the distal and proximal direction; wherein the clamp arms are each coupled to the distal end of the control wire and wherein the clamp device is actuable to open and close the clamp arms.

17 Claims, 32 Drawing Sheets

(51) Int. Cl.
*A61B 17/00* (2006.01)
*A61B 17/12* (2006.01)

(58) Field of Classification Search
CPC ........... A61B 2017/12004; A61B 2017/00477;
A61B 2090/037
See application file for complete search history.

(56) References Cited

U.S. PATENT DOCUMENTS

| | | | |
|---|---|---|---|
| 2010/0152753 A1 | 6/2010 | Menn et al. | |
| 2014/0171973 A1* | 6/2014 | Zhu .................... | A61B 17/1285 |
| | | | 606/144 |
| 2016/0302794 A1 | 10/2016 | Torp et al. | |
| 2019/0090882 A1* | 3/2019 | Estevez .............. | A61B 17/1285 |

FOREIGN PATENT DOCUMENTS

| | | |
|---|---|---|
| CN | 112603396 A | 4/2021 |
| CN | 213821584 U | 7/2021 |
| EP | 1328199 B1 | 6/2018 |
| WO | WO2020211725 A1 | 10/2020 |
| WO | WO2021004107 A1 | 1/2021 |

* cited by examiner

MEDICAL DEVICE FOR CAUSING HEMOSTASIS OF BLOOD VESSEL

This application is the national phase of International Application No. PCT/CN2022/078084, titled "MEDICAL DEVICE FOR CAUSING HEMOSTASIS OF BLOOD VESSEL", filed on Feb. 25, 2022, the entire disclosure of which is incorporated herein by reference.

TECHNICAL FIELD

The present disclosure relates to a medical device for causing the hemostasis of a blood vessel for use through an endoscope.

BACKGROUND

Medical devices of this kind are known for example from EP 1328199 B1 and in particular used to treat gastrointestinal bleedings. Specifically, such devices are used to set clamps or clips to pinch a bleeding vessel applying sufficient constrictive force to the blood vessel so as to limit or interrupt blood flow there through.

The medical device known from EP 1328199 B1 comprises a handle and a sheath, which is attached to the handle. A control wire extends through the sheath and can be actuated by an actuator, which is coupled to the proximal end of the control wire to reversibly move the control wire in the distal and proximal directions. The medical device further includes a clamp device including a sleeve provided on the distal end of the sheath and a clip with two clamp arms is coupled to the distal end of the control wire by means of a J-hook. The clamp arms cooperate with the sleeve in such a way, that the clamp arms engage the front edge of the sleeve to be elastically deformed inwardly, thus being closed, when the control wire is pulled in the proximal direction, whereas the clamp arms are distally pushed out of the sleeve and automatically reopen due to their elastic restoring force, when the control wire is pushed in the distal direction. Since the clamp device can be repeatedly opened and closed, setting of the clamp device is possible in an easy way.

Once the clamp device is set at the correct position, the clamp arms must be locked in their closed state. For this purpose, openings are provided at the clamp arms, into which corresponding protrusions formed in the inner surface of the sleeve can engage. In order to lock the clamp arms in their closed state, the control wire is pulled in the proximal direction so far, that the protrusions come into engagement with the openings formed in the clamp arms.

Furthermore, the clamp device with the clamp arms and the sleeve can be disconnected from the rest of the medical device. In order to do so, the control wire is further pulled back, when the clamp device is completely closed, so that the J-hooks brake and thus the connection between the clamp arms and the control wire is interrupted. Moreover, by further pulling back the control wire, a retainer, which connects the control wire with the sleeve, is actuated in order to disconnect the retainer and thus the control wire from the sleeve.

SUMMARY

In view of this prior art it is the object of the present disclosure to provide a medical device of the above-mentioned kind that it is easy to operate as well as easy to manufacture and assemble and that works in a reliable manner.

This object is solved by a medical device that the pivot pin protrudes laterally on both sides from the clamp arms and the distal end of the control wire, and in that two locking noses are provided on the clamp housing extending into the interior space of the clamp housing, wherein the locking noses are designed in such a way that they allow the pivot pin to pass them in the proximal direction but prevent passing of the pivot pin in the distal direction in order to lock the clamp arms in a closed state.

A medical device for causing the hemostasis of blood vessel comprises:

a handle;

a sheath device, which is attached to the handle;

a clamp device including a clamp housing defining a longitudinal direction with a clamp base in particular in the form of a sleeve provided on the distal end of the sheath device and at least two, in particular exactly two clamp arms, said clamp housing defining an interior space;

a control wire extending through the sheath device and reversibly movable in the distal and proximal direction; and an actuator coupled to the proximal end of the control wire and actuable to reversibly move the control wire in the distal and proximal direction;

where the clamp arms are each coupled to the distal end of the control wire and where the clamp device is actuable to open and close the clamp arms by a movement of the control wire such that a movement of the control wire in a proximal direction is translated into a closing movement of the clamp arms and a movement of the control wire in the distal direction is translated into an opening movement of the clamp arms;

where the clamp arms are coupled to the distal end of the control wire via a pivot pin extending through corresponding through-holes provided in the proximal end sections of the clamp arms and being held releasably at the distal end of the control wire, where the pivot pin protrudes laterally on both sides from the clamp arms and the distal end of the control wire and two locking noses are provided on the clamp housing extending into the interior space of the clamp housing, where the locking noses are designed in such a way that they allow the pivot pin to pass them in the proximal direction but prevent passing of the pivot pin in the distal direction in order to lock the clamp arms in a closed state.

The present disclosure is based on the consideration to provide locking noses protruding into the interior space of the clamp housing in such a way, that the pivot pin is locked proximally with respect to the locking noses once the pivot pin has passed the locking noses. In this way, a stable and reliable locking of the clamp arms in their closed state can be achieved. Preferably, the pivot pin passes the locking noses in such a way that the end faces of the pivot pin come into contact with the locking noses. Accordingly, the locking noses may be provided on opposite sides of the interior space. Consequently, the pivot pin may pass over the locking noses by means of an elastic deformation and returns to its original shape once it has passed the locking noses.

According to a preferred embodiment of the present disclosure, it may be provided that each locking nose has on its distal side an inclined surface with respect to the longitudinal direction of the clamp housing and on its proximal side a surface extending perpendicular to the longitudinal direction. Preferably, the inclination angle of the inclined surface is at minimum 30° and/or at maximum 60°, preferably 45° with respect to the longitudinal direction of the clamp housing. Accordingly, it is provided, that the locking noses have on their distal side inclined surfaces, so that the interior space is tapering in this region in order to allow the pivot pin to pass the locking noses by elastic and/or plastic deformation. Once the pivot pin has passed the locking noses, passing from the proximal into the distal direction is not possible since the surfaces on the proximal side of the locking noses extend perpendicular to the longitudinal direction. In this way, the pivot pin is safely locked proximally to the locking noses and thus the clamp arms remain in their closed state.

In order to allow an elastic and/or plastic deformation of the pivot pin, when passing the locking noses, the pivot pin is preferably of tubular shape. The pivot pin may be made of a metallic material, in particular of stainless steel, or a plastic material.

According to a further embodiment, the clamp housing has on its inner surface two sliding grooves extending in the longitudinal direction and arranged opposite each other in such a way that the end sections of the pivot pin engage into the sliding grooves. In this way, it is ensured, that the pivot pin cannot rotate about the longitudinal direction of the clamp housing relative to the clamp housing. In other words, a torque-proof connection between the pivot pin and the clamp housing with respect to the longitudinal direction is realized. The sliding grooves may have a rectangular cross-section.

The locking noses may project from the ground of the respective sliding groove into the sliding groove. Accordingly, the locking noses can be entirely arranged within the sliding groove. In this way, it is avoided that the locking noses interfere with other components arranged or moved in the interior space of the clamp housing. According to a preferred embodiment, the locking noses extend over the entire width of the respective sliding groove.

The clamp arms may be provided as separate elements, which are coupled to the distal end of the control wire in a pivotal manner a round common pivot axis defined by the pivot pin.

Preferably, the clamp housing comprises two bearing arms extending in the distal direction from the clamp base, wherein, in particular, a guide pin is held between the two bearing arms. Accordingly, each clamp arm can be provided with a guide groove and the guide grooves of the clamp arms partially overlap each other, and the guide pin, which is attached to the clamp housing, can extend through the guide grooves in the overlapping parts thereof, so that by the engagement of the guide pin and the guide grooves, a movement of the control wire in the proximal direction is translated into a closing movement of the clamp arms and a movement of the control wire in the distal direction is translated into an opening movement of the clamp arms around the pivot axis.

The clamp housing may comprise a central passage opening in particular in the clamp base, which central passage opening preferably has a rectangular cross-section. Accordingly, the interior space of the clamp housing may be defined by the central passage opening and the space between the bearing arms.

Furthermore, a disengaging arrangement may be provided, which allows disconnecting the clamp arms from the control wire when the clamp arms are locked in the closed state and the control wire is further pulled in the proximal direction. In other words, it must be ensured, that the clamp arms can be disconnected from the control wire when the clamp arms are in the closed state and the clamp device should be released from the rest of the medical device.

In concrete terms, the control wire can include a coupling head at its distal end, the coupling head comprising at least one pair of holding arms, which holding arms are moveable between a fixing position, in which the holding arms encompass the pivot pin, thus holding the pivot pin in particular in a form-fit manner, and a disengaging position, in which the holding arms are spread apart from each other, thus releasing the pivot pin, wherein the holding arms are biased towards their disengaging position, and the inner contour of the clamp housing cooperates with the holding arms in such a way that the holding arms are pressed towards each other into their fixing position as long as the holding arms extend into a distal section of the clamp housing, and that the holding arms return automatically into their disengaging position, when the control wire is pulled in the proximal direction such that the holding arms reach a proximal section of the clamp housing.

In other words, a specific coupling head is provided at the distal end of the control wire. This coupling head comprises at least two holding arms which engage around the pivot pin protruding laterally from the clamp arms as long as the clamp arms are coupled to the control wire. The holding arms of the coupling head of the control wire are automatically held in their fixing position as long as the holding arms extend into a distal section of the clamp housing. When the clamp arms are closed and in particular locked in their closed state and the control wire is further pulled back, the holding arms reach a proximal section in particular having an enlarged opening size compared to the distal section. Due to the elastic restoring force of the holding arms, they return automatically into their disengaging position when the holding arms reach the enlarged proximal section of the clamp housing, thus releasing the pivot pin.

In concrete terms, the inner contour of the clamp housing may comprise one retaining groove assigned to each pair of holding arms, wherein the retaining groove receives the holding arms between its side walls such that the holding arms abut against the side walls and are held in their fixing position as long as the holding arms extend into the retaining groove, and each retaining groove leads proximally into an enlarged proximal section of the clamp housing having an enlarged opening size compared to the retaining groove so that the holding arms return automatically into their disengaging position, when the control wire is pulled in the proximal direction such that the holding arms reach the enlarged proximal section. In other words, a retaining groove extending in the longitudinal direction of the clamp housing, which may in particular have a rectangular cross-section, serves to receive the holding arms of the coupling head and keeps them in their fixing position, as long as the holding arms are positioned in the retaining groove. Accordingly, one holding arm of the pair of holding arms abuts against one side wall of the retaining groove and the other holding arm against the opposite side wall. In this way, the holding arms are received in the retaining grooves in a very space-saving manner.

According to a further embodiment, the coupling head comprises exactly two pairs of holding arms which are arranged on laterally opposite sides of the clamp arms and one retaining groove is correspondingly arranged on both sides of the clamp arms in the clamp housing. The coupling head may have a U-shaped or bifurcated structure at its distal end.

Preferably, the sliding grooves are arranged in the retaining grooves, in particular in the grounds of the retaining grooves. Accordingly, the retaining grooves, which are arranged opposite each other, form a basically rectangular cross-section, in particular a quadratic cross-section of the interior space of the clamp housing. In laterally opposite faces of this interior space, the sliding grooves, which receive the ends of the pivot pin, may be arranged.

The transition between the enlarged proximal section and the retaining grooves may be formed as a step. Such a step correlates with an immediate change of the opening size between the enlarged proximal section and the retaining groove, so there is a defined moment in which the pivot pin is uncoupled from the control wire. Furthermore, it is not possible to bring the holding arms back into their fixing position once they have reached their disengaging position. In this way, incorrect use of the medical device can be excluded.

Preferably, the step is arranged with respect to the locking noses in such a way that the pivot pin passes the locking noses before the holding arms of the coupling head reach the enlarged proximal section and return into their disengaging position. This embodiment is based on the consideration that it is necessary to first lock the clamp arms in their closed state, before the clamp arms are separated from the control wire. In this way, a safe and reliable operation can be guaranteed. Accordingly, at first the pivot pin must pass the locking noses before the holding arms extending until a position distally from the pivot pin can return into their disengaging position. In concrete terms, the step may be arranged distally from the locking noses.

Recesses for receiving the pivot pin may be formed in the surfaces of the holding arms facing towards each other, wherein the recesses preferably extend over the entire thickness of the respective holding arm and/or preferably have an at least substantially semicircular cross-section. In this way, a form-fit connection between the holding arms—when they are in their fixing position—and the pivot pin can be realized. A semicircular cross-section of the recesses allows a pivoting movement of the pivot pin in the recesses.

According to preferred embodiment of the present disclosure, the holding arms of each pair are present in a one-piece design, so that the holding arms are elastically deformable between their fixing position and their disengaging position. In other words, the holding arms of one pair of holding arms are not formed as a separate element, but as one piece arranged at the distal end of the control wire, wherein the holding arms are elastically deformable between their fixing position and their disengaging position.

BRIEF DESCRIPTION OF DRAWINGS

Embodiments of the present disclosure will in the following be described making reference to the attached drawing. In this drawing shows.

Figure 1:
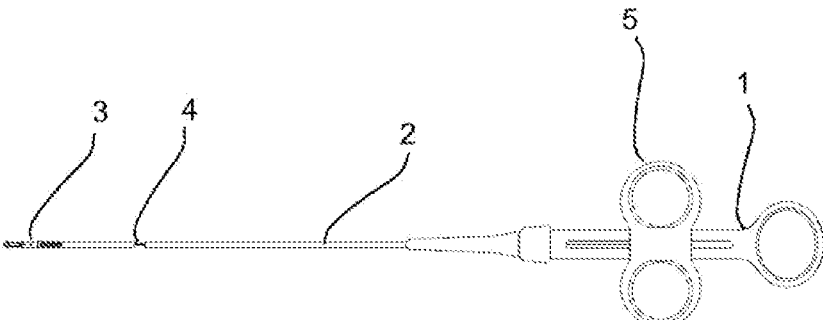
FIG. 1 a front view of a medical device according to a first embodiment of the present disclosure.
Figure 2:
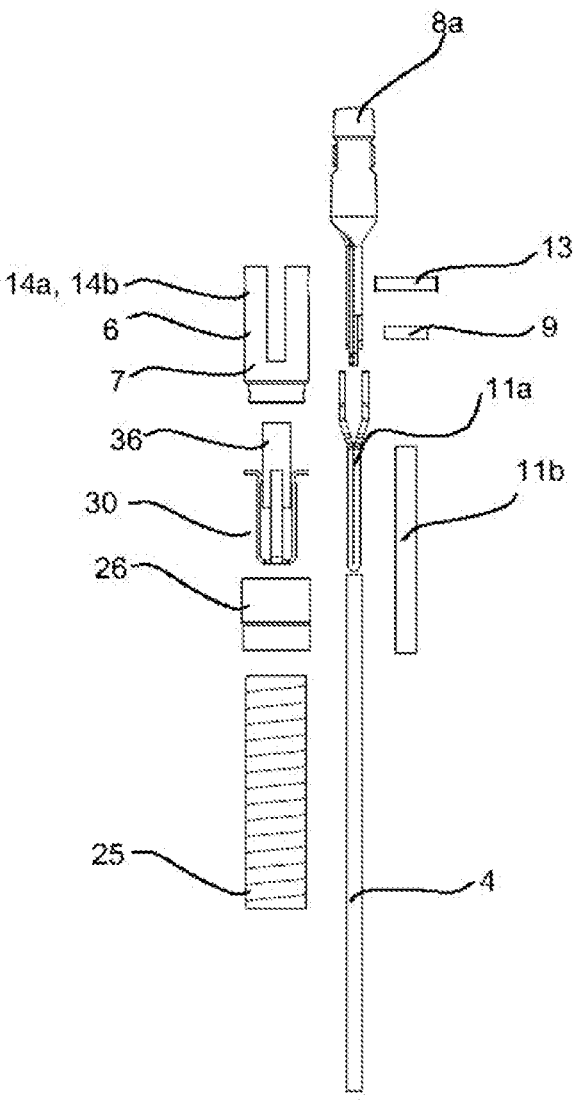
FIG. 2 an exploded view of the distal end of the medical device of FIG. 1.
Figure 3:
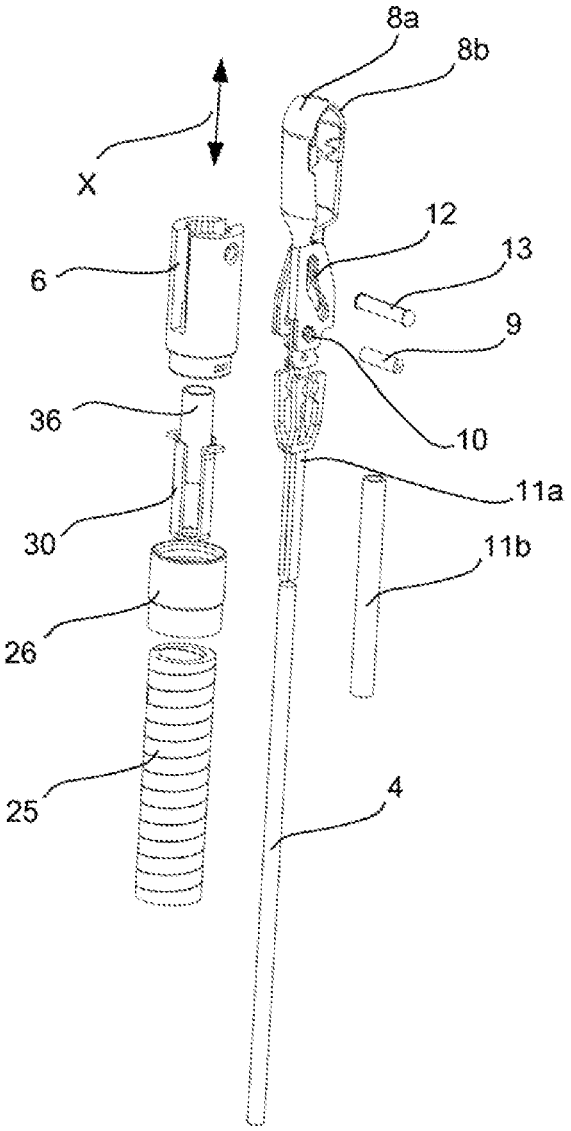
FIG. 3 a perspective exploded view of the distal end of the medical device of FIG. 1.
Figure 4:
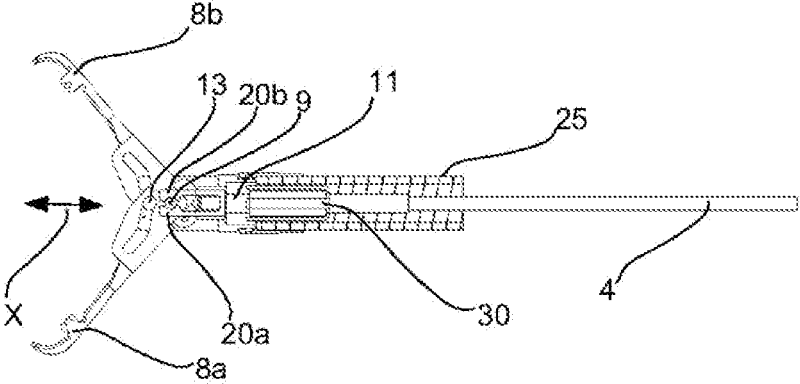
FIG. 4 a cross-sectional view of the distal end of the medical device of FIG. 1 with open clamp arms.
Figure 5:
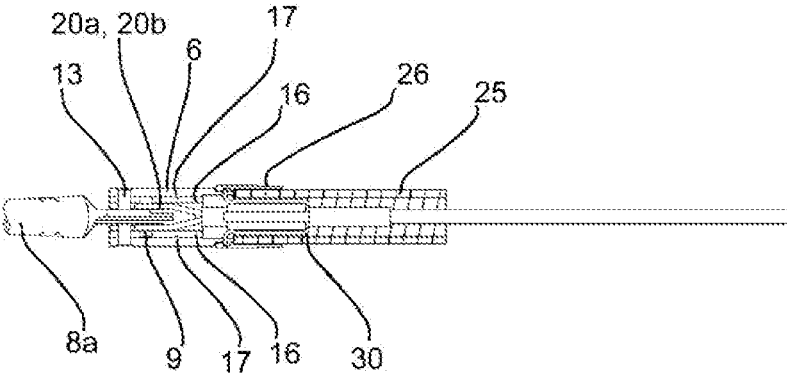
FIG. 5 a cross-sectional view of the distal end of the medical device of FIG. 1 with open clamp arms in another sectional plane.
Figure 6:
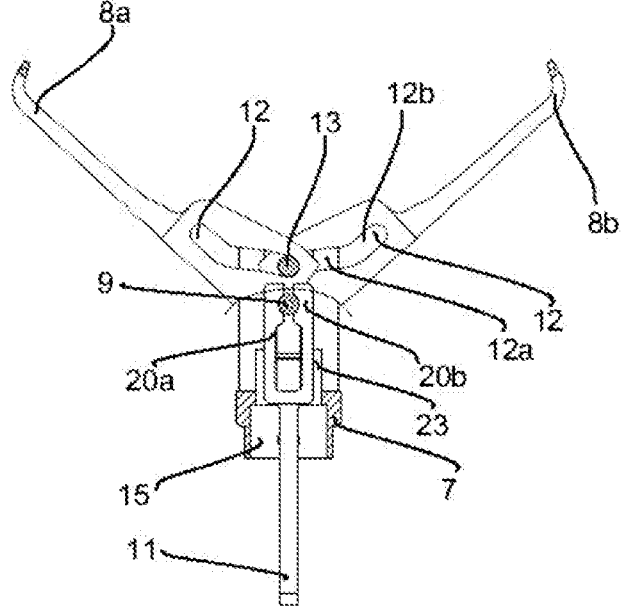
FIG. 6 another cross-sectional view of the distal end of the medical device of FIG. 1 with open clamp arms.
Figure 7:
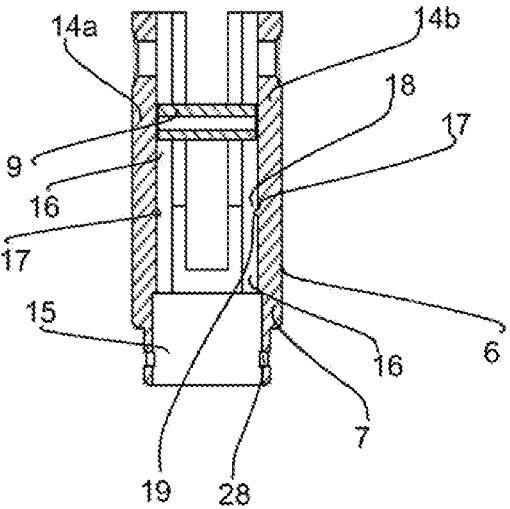
FIG. 7 the clamp base and the pivot pin of the medical device of FIG. 1 in a cross-sectional view with open clamp arms.
Figure 8:
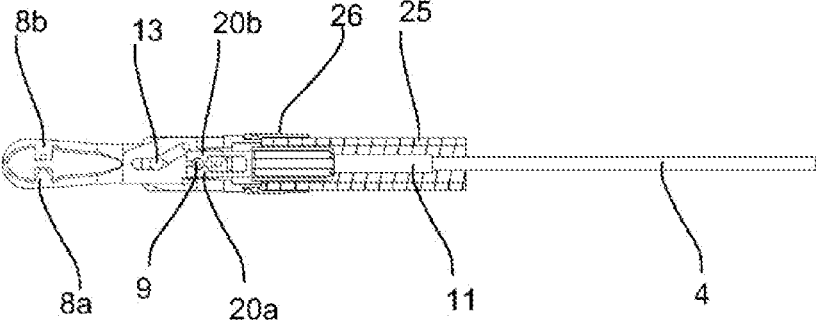
FIG. 8 a cross-sectional view of the medical device of FIG. 1 with closed clamp arms.
Figure 9:
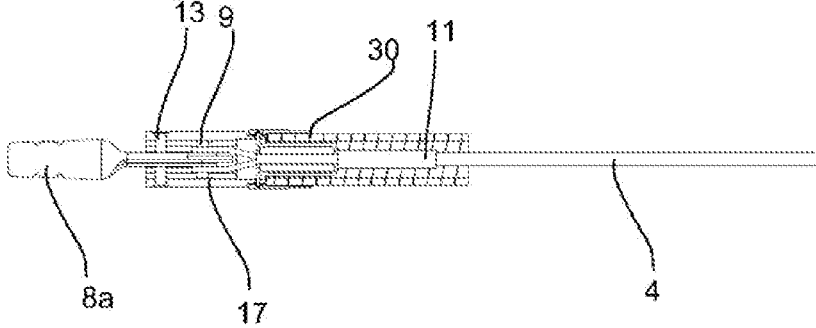
FIG. 9 a cross-sectional view of the distal end of the medical device of FIG. 1 with closed clamp arms in another sectional plane.
Figure 10:
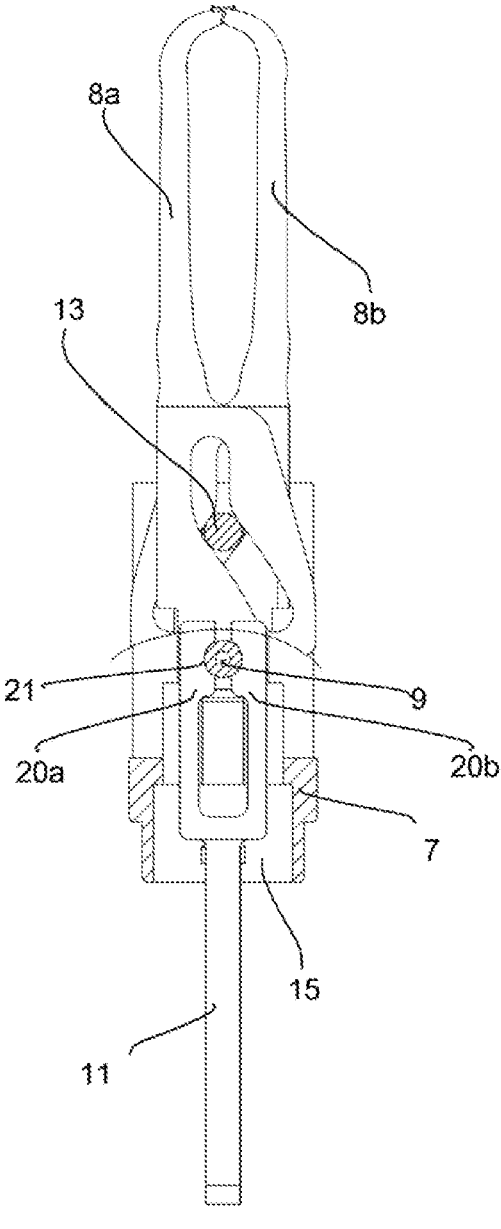
FIG. 10 a cross-sectional view of the distal end of the medical device of claim 1 with closed clamp arms.
Figure 11:
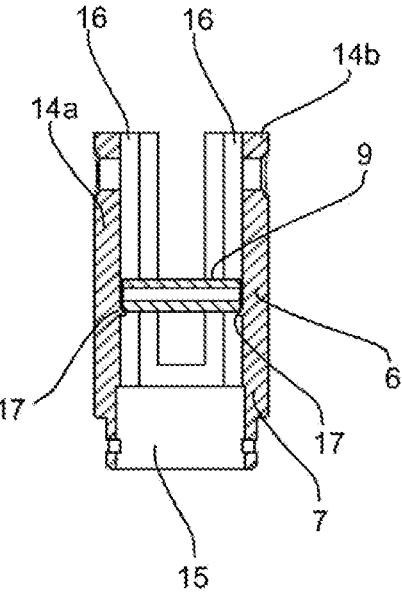
FIG. 11 a cross-sectional view of the clamp base and the pivot pin of the medical device of FIG. 1 with closed clamp arms.
Figure 12:
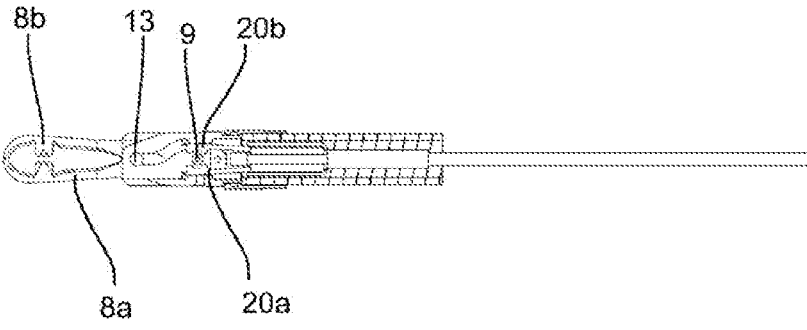
FIG. 12 a cross-sectional view of the distal end of the medical device of FIG. 1 with clamp arms locked in their closed state.
Figure 13:
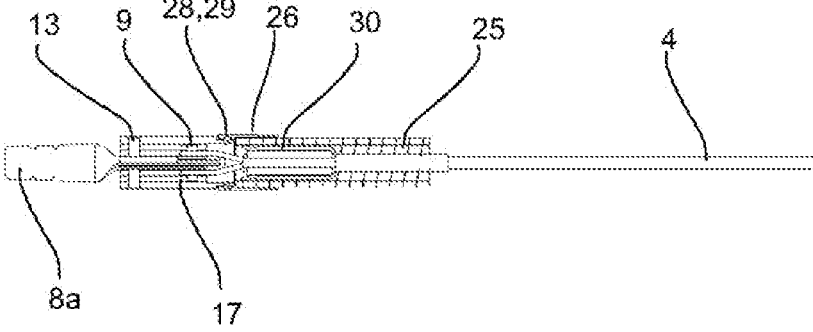
FIG. 13 a cross-sectional view of the distal end of the medical device with clamp arms locked in their closed state in another sectional plane.
Figure 14:
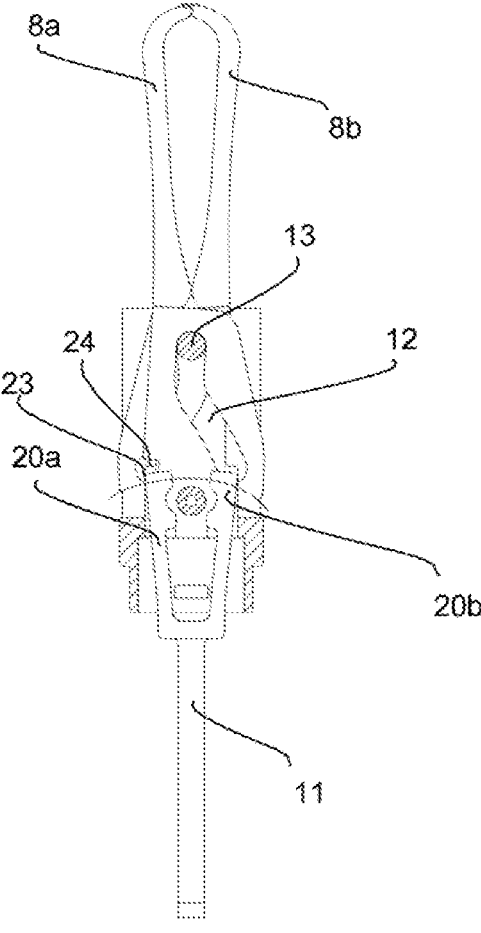
FIG. 14 a cross-sectional view of the distal end of the medical device of claim 1 with clamp arms locked in their closed state.
Figure 15:
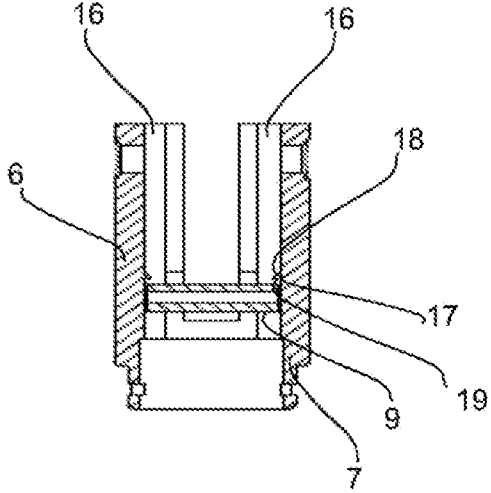
FIG. 15 a cross-sectional view of the clamp base and the pivot pin of the medical device of FIG. 1 with clamp arms locked in their closed state.
Figure 16:
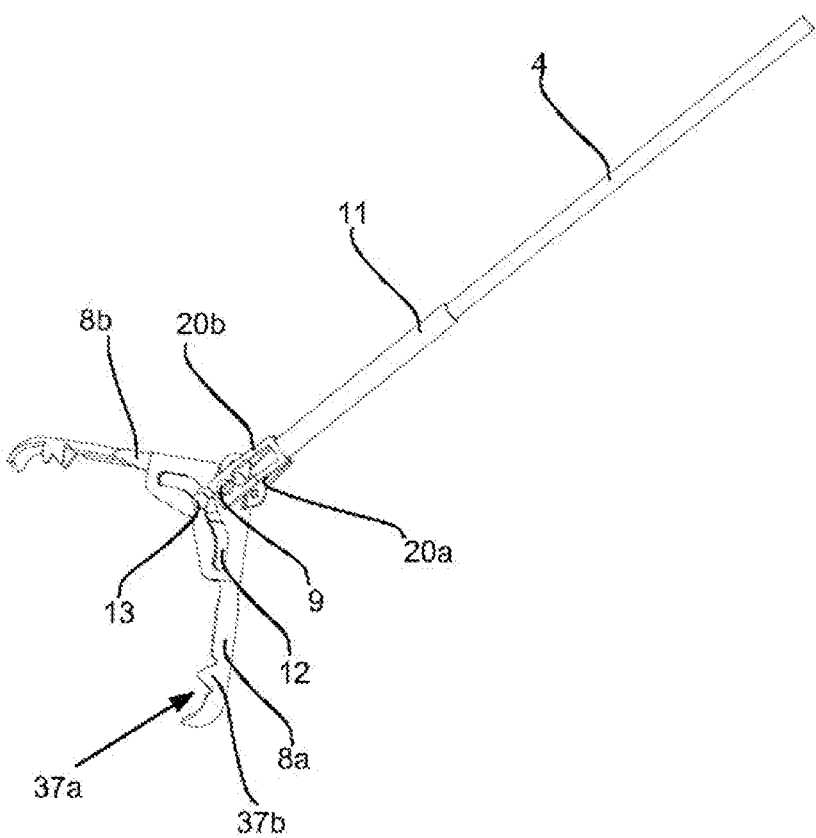
FIG. 16 a partial perspective view of the distal end of the control wire and the clamp arms.
Figure 17:
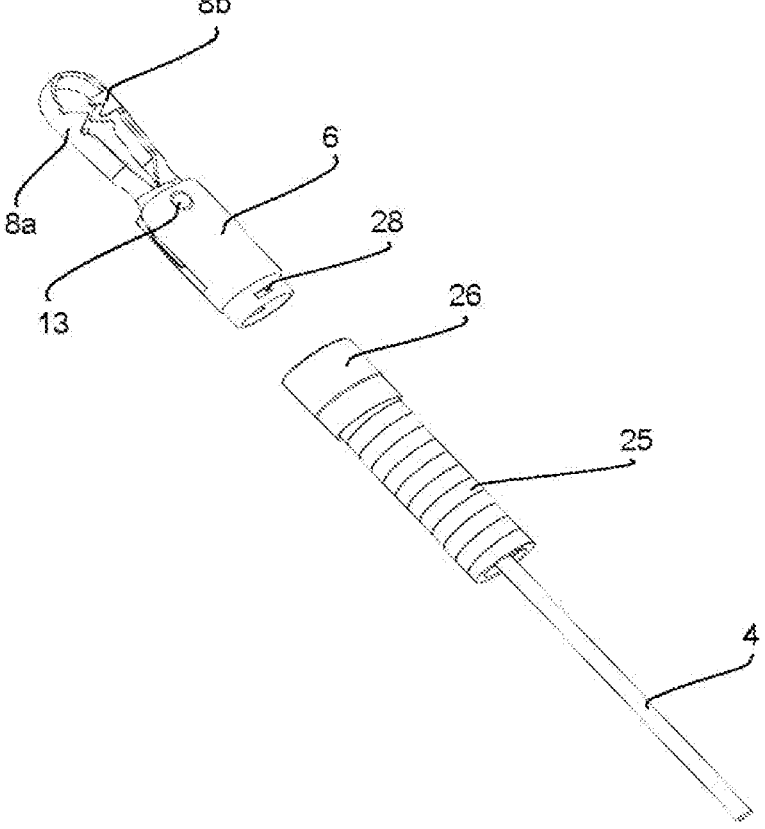
FIG. 17 a partial perspective view of the distal end of the medical device with the clamp device released from the sheath device.
Figure 18:
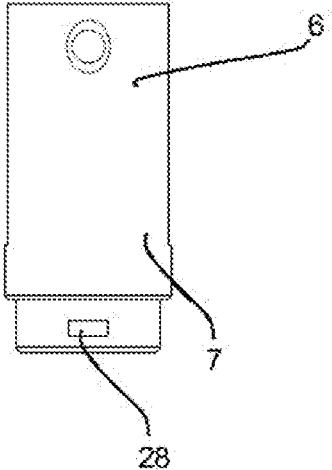
FIG. 18 a front view of the clamp base.
Figure 19:
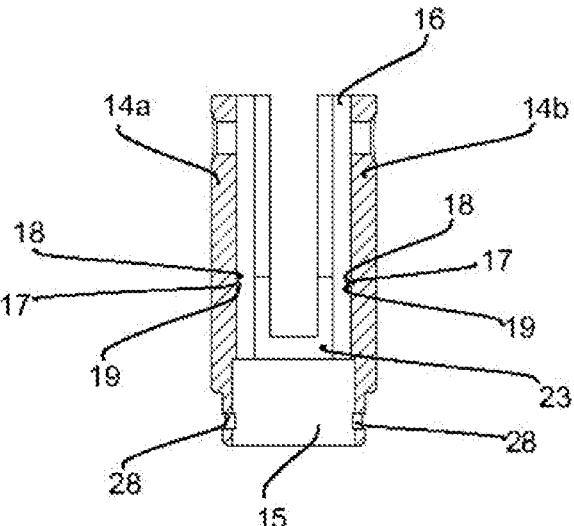
FIG. 19 a longitudinal sectional view of the clamp base.
Figure 20:
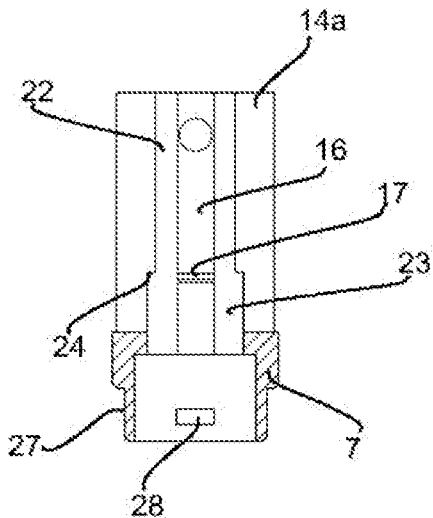
FIG. 20 another longitudinal sectional view of the clamp base.
Figure 21:
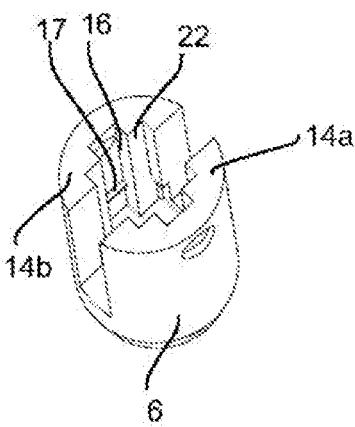
FIG. 21 a perspective view of the clamp base.
Figure 22:
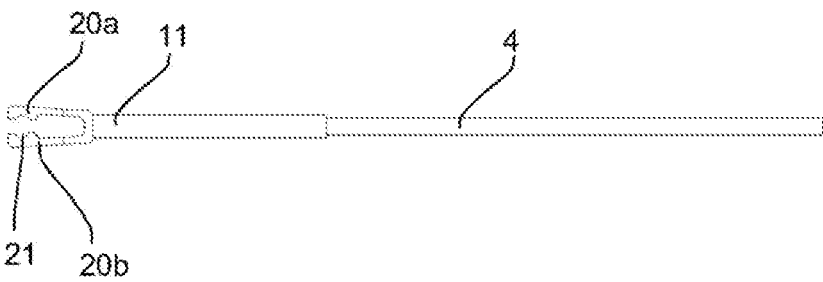
FIG. 22 a side view of the distal end of the control wire with the coupling head.
Figure 23:
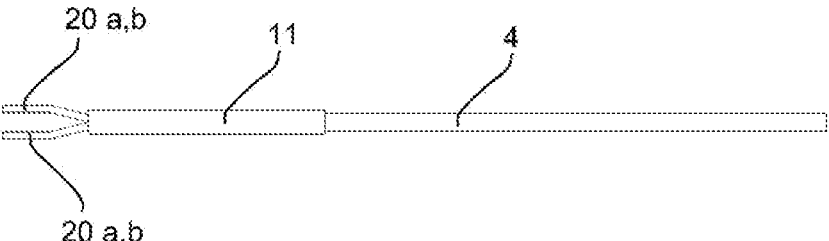
FIG. 23 a top view of the distal end of the control wire.
Figure 24:
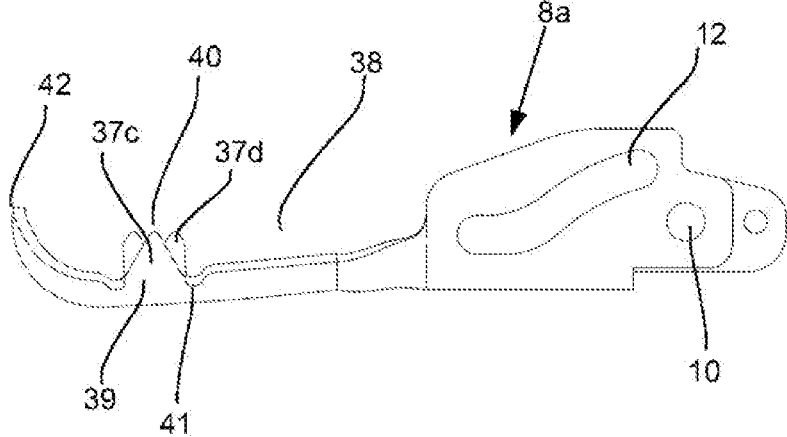
FIG. 24 a side view of a clamp arm of the device of FIG. 1.
Figure 25:
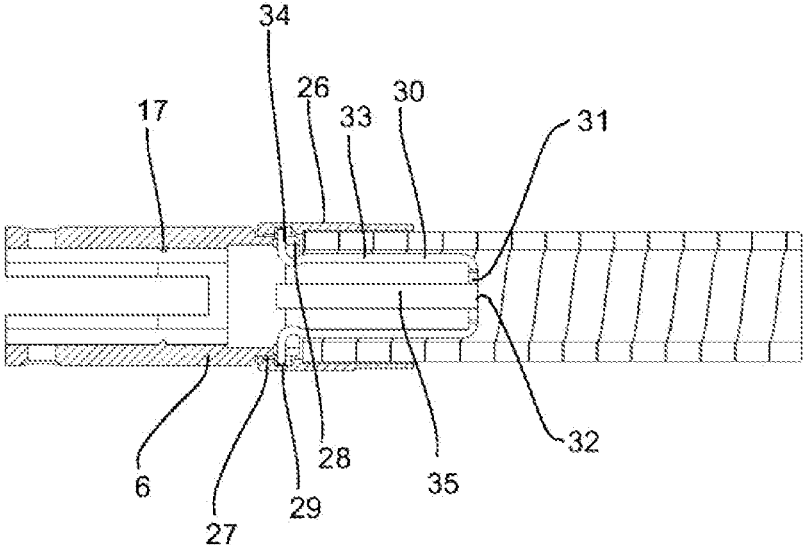
FIG. 25 a partial cross-sectional view of the distal end of the medical FIG. 25 device of FIG. 1.
Figure 26:
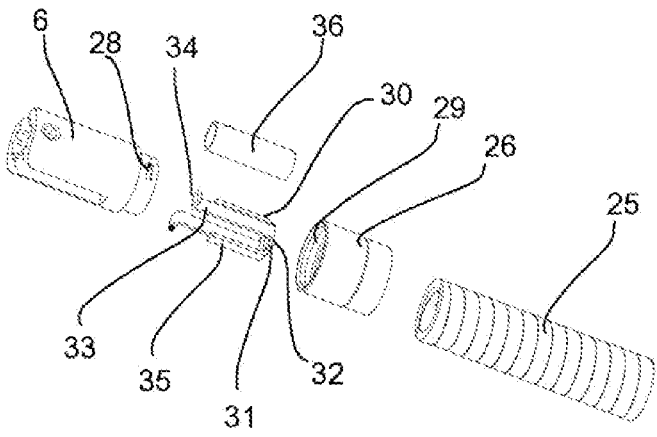
FIG. 26 a partial exploded view of the distal end of the medical device of FIG. 1 showing the release mechanism of the clamp base and the sheath device.

List of Reference Numerals in the Drawings 1 handle
2 sheath device
3 clamp device
4 control wire
5 actuator
6 clamp housing
7 clamp base
8a, 8b clamp arm
9 pivot pin
10 through-hole
11 coupling head
11a sheet-like part
11b pressing tube
12 guide groove
12a curved section
12b straight section
13 guide pin
14a, 14b bearing arm
15 central passage opening
16 sliding groove
17 locking nose
18 inclined surface
19 surface
20a, 20b holding arm
21 recess
22 retaining groove
23 enlarged proximal section
24 step
25 sheath
26 connect tube
27 overlapping section
28 through-aperture
29 ring groove
30 connecting element
31 main section
32 central opening
33 connecting arm
34 engagement portion
35 guiding arm
36 intermediate tube
37a-d barb
38 grasping section
39 V-shaped protrusion
40 V-shaped recess
41 rounded notch
42 engagement contour
43 holding aperture
44 straight section
45 inwardly bulged section
46 protrusion
X longitudinal direction

DESCRIPTION OF EMBODIMENTS

FIGS. 1 to 26 show a first embodiment of a medical device according to the present disclosure. The medical device is used to set clamps for causing hemostasis of blood vessels located along the gastrointestinal tract, wherein the clamps are delivered to a target site through an endoscope.

The medical device comprises a handle 1, a sheath device 2, which is attached to the handle 1, and a clamp device 3, which is provided on the distal end of the sheath device 2.

A control wire 4 extends through the sheath device 2 and is at its proximal end connected to an actuator 5, which is slidingly held on the handle 1 and can be actuated to reversibly move the control wire 4 in the distal and proximal directions. The actuator 5 and the handle 1 are designed in such a way that the control wire 4 can be rotated relative to the sheath device 2 about its longitudinal axis.

The clamp device 3 comprises a clamp housing 6 with a clamp base 7 formed as a sleeve and two clamp arms 8a, 8b, which are each coupled to the distal end of the control wire 4. Specifically, the two clamp arms 8a, 8b are separate elements/components that are coupled to the control wire 4 by means of a pivot pin 9, which is of tubular shape. For this purpose, the pivot pin 9 extends through corresponding through-holes 10 provided in the proximal end sections of the clamp arms 8a, 8b and is releasably held by a coupling head 11 formed at the distal end of the control wire 4.

The two clamp arms 8a, 8b are coupled to the distal end of the control wire 4 so that they can be rotated around a common pivot axis formed by the pivot pin 9 in order to open and close them. Each clamp arm 8a, 8b is provided with a guide groove 12, and the guide grooves 12 of the clamp arms 8a, 8b partially overlap each other. Each guide groove 12 comprises a proximal curved section 12a and a distal straight section 12b. The clamp device 3 further comprises a guide pin 13, which is attached to the clamp housing 6 and extends through the guide grooves 12 in the overlapping parts thereof, so that by the engagement of the guide pin 13 and the guide grooves 12 a movement of the control wire 4 in the proximal direction is translated into a closing movement of the clamp arms 8a, 8b. A movement of the control wire 4 in the distal direction is translated into an opening movement of the clamp arms 8a, 8b around the pivot axis. In the present embodiment, the guide pin 13 is held between two bearing arms 14a, 14b of the clamp housing 6 extending in the distal direction from the clamp base 7 forming a bifurcated structure, the clamp arms 8a, 8b being arranged between those bearing arms 14a, 14b. The clamp housing 6 has an interior space presently defined by a central passage opening 15 formed in the clamp base 7 and the space between the bearing arms 14a, 14b.

The clamp housing 6 has on its inner surface two sliding grooves 16 extending in the longitudinal direction of the clamp housing 6 and arranged opposite each other in such a way that the end sections of the pivot pin 9 engage into the sliding groves 16. The sliding grooves 16 have a rectangular cross-section. In order to lock the clamp arms 8a, 8b in a closed state, as it is shown in FIGS. 12 to 15, two locking noses 17 are provided on the clamp housing 6. Presently, the locking noses 17 project from the ground of the respective sliding groove 16 into the sliding groove 16 and extend over the entire width of the respective sliding groove 16. The locking noses 17 are designed in such a way that they allow the pivot pin 9 to pass them in the proximal direction but prevent passing of the pivot pin in the distal direction in order to lock the clamp arms 8a, 8b in a closed state. For this purpose, each locking nose 17 has on its distal side an inclined surface 18 having an inclination angle of 45° with respect to the longitudinal direction X of the clamp base 7 and on its proximal side a surface 19 extending perpendicular to the longitudinal direction X.

The medical device further comprises a disengaging arrangement, which allows disconnecting the clamp arms 8a, 8b from the control wire 4, when the clamp arms 8a, 8b are locked in the closed state and the control wire 4 is further pulled in the proximal direction.

For this purpose, the coupling head 11 has a bifurcated holding structure comprising two pairs of holding arms 20*a*, 20*b*, which are arranged on laterally opposite sides of the clamp arms 8*a*, 8*b*. The holding arms 20*a*, 20*b* are movable between a fixing position, which is for example shown in FIGS. 4 to 11, and a disengaging position, which is for example shown in FIGS. 12 to 15. In the fixing position, the holding arms 20*a*, 20*b* encompass the pivot pin 9, thus holding the pivot pin 9 in a form-fit manner. In concrete terms, recesses 21 with a semicircular cross-section are formed in the surfaces of the holding arms 20*a*, 20*b* facing towards each other. The pivot pin 9 is held in these recesses 21 in the fixing position of the holding arms 20*a*, 20*b*. In their disengaging position, the holding arms 20*a*, 20*b* are spread apart from each other, thus releasing the pivot pin 9. The holding arms 20*a*, 20*b* are biased towards their disengaging position. As it is visible in particular in FIGS. 2 and 3, the coupling head 11 is formed by a sheet-like part 11*a* forming the two pairs of holding arms and a pressing tube 11*b*, by means of which the sheet-like part 11*a* is connected to the adjacent proximal part of the control wire 4.

The inner contour of the clamp housing 6 cooperates with the holding arms 20*a*, 20*b* in such a way that the holding arms 20*a*, 20*b* are pressed towards each other into their fixing position as long as the holding arms 20*a*, 20*b* extend into a distal section of the clamp housing 6. Presently, the inner contour of the clamp housing 6 comprises one retaining groove 22 assigned to each pair of holding arms 20*a*, 20*b* and open towards the distal end of the clamp housing 6. Accordingly, in total two retaining grooves 22 having a rectangular cross-section are located on opposite sides of the interior space of the clamp housing 6. The retaining grooves 22 receive the holding arms 20*a*, 20*b* between their side walls such that the holding arms 20*a*, 20*b* abut against the side walls and are pressed into their fixing position against their restoring force as long as the holding arms 20*a*, 20*b* extend into the retaining groove 22.

The retaining grooves 22 lead proximally into an enlarged proximal section 23 of the clamp housing 6 having an enlarged opening size compared to the retaining groove 22. The transition between the enlarged proximal section 23, which has a substantially rectangular cross-section, and the retaining groove 22 is formed as step 24. Presently, the enlarged proximal section 23 extends over the central passage opening 15 and a proximal part of the bearing arms 14*a*, 14*b*. Accordingly, the holding arms 20*a*, 20*b* return automatically into their disengaging position due to their restoring force, when the control wire 4 is pulled in the proximal direction such that the holding arms 20*a*, 20*b* reach the enlarged proximal section 23.

Presently, the step 24 is arranged with respect to the locking noses 17 in such a way that the pivot pin 9 passes the locking noses 17 before the holding arms 20*a*, 20*b* of the coupling head 11 reach the enlarged proximal section 23 and return into their disengaging position. In concrete terms, the step 24 is arranged distally from the locking noses 17. Accordingly, the holding arms 20*a*, 20*b* return into their disengaging position before the guide pin 13 reaches the distal end of the straight section 12*b* of the guide grooves 12.

The sheath device 2 includes a coiled sheath 25, which is connected to the handle 1, and a connect tube 26 fixedly connected, presently welded to the distal end of the sheath 25, so that the sheath 25 and the connect tube 26 form an inseparable unit.

The clamp housing 6 is directly and releasably connected to the connect tube 26 in such a way that the clamp housing 6 can be rotated relative to the connect tube 26 about the longitudinal axis. In concrete terms, this connection is realized by a push-in connection, thus forming an overlapping section 27 of the connect tube 26 and the clamp housing 6. In the embodiment shown in FIGS. 1 to 26, the clamp housing 6 is pushed into the connect tube 26, so that the clamp housing 6 forms an inner element and the connect tube 26 forms an outer element. Two through-apertures 28 are formed in the overlapping section 27 of the clamp housing 6 and a corresponding ring groove 29 facing inwardly is formed in the overlapping section 27 of the connect tube 26.

Presently, one connecting element 30 is provided which engages through the through-apertures 28 into the ring groove 29 in order to connect the clamp housing 6 to the sheath device 2 such that the clamp housing 6 can be rotated relative to the connect tube 26 of the sheath device 2. In concrete terms, the connecting element 30 comprises a proximal main section 31 in the form of a disc having a central opening 32. The control wire 4 passes through this central opening 32. Two connecting arms 33 arranged opposite each other in the circumferential direction extend distally from the main section 31, wherein engagement portions 34 are formed at the distal ends of the connecting arms 33 and extend radially outwardly through the through-apertures 28 into the ring groove 29. Furthermore, the connecting element comprises two guiding arms 35 extending distally from the main section 31. The guiding arms 35 are arranged between the connecting arms 33 in the circumferential direction.

A release arrangement cooperating with the connecting element 30 is provided and can be actuated by moving the control wire 4 in the proximal direction, when the clamp arms 8*a*, 8*b* have been closed and the control wire 4 has been uncoupled from the clamp device 3 in order to bring the connecting element 30 out of engagement from the ring groove 29 of the connect tube 26. In concrete terms, the release arrangement comprises an intermediate tube 36 enclosing the control wire 4 and arranged between the connecting element 30 and the coupling head 11 of the control wire 4.

The intermediate tube 36 is designed such that it can push against the main section 31 of the connecting element 30. Accordingly, the intermediate tube 36 can push the connecting element 30 in the proximal direction when the control wire 4 is moved in the proximal direction and the clamp arms 8*a*, 8*b* have been closed. In this way, the engagement portions 34 can be brought out of engagement from the ring groove 29 formed in the connect tube 26, thus releasing the clamp housing 6 from the connect tube 26, as it is shown for example in FIG. 13.

In use, the clamp device 3 is delivered to the target site through an endoscope and the clamp device 3 is fixed at a predetermined position on the target site to a blood vessel. For this purpose, the clamp device 3 can be rotated relative to the sheath device 2 by rotating the control wire 4 relative to the sheath device 2. In order to pinch the blood vessel, the clamp arms 8*a*, 8*b* can be repeatedly opened and closed by moving the control wire 4 in the distal and proximal direction by means of the actuator 5.

In order to improve the grasping of tissue positioned between the clamp arms 8*a*, 8*b* and to minimize the risk of loosening the clamp device 3 when fixed to tissue inside the body of a patient, each clamp arm 8*a*, 8*b* comprises two barbs 37*a*, 37*b*, 37*c*, 37*d* arranged on laterally opposite sides of the clamp arm 8*a*, 8*b* in a grasping section 38. The barbs 37*a*, 37*b*, 37*c*, 37*d* are formed such that each barb points in the direction of a corresponding, opposite barb of the other clamp arm 8*a*, 8*b*. For example, on FIG. 24 it is visible that the clamp arm 8*b* comprises two barbs 37*c*, 37*d* pointing towards the other clamp arm 8*a*. The barb 37*c* comprises a clamping contour in the form of a V-shaped protrusion 39, wherein the barb 37*d* comprises a clamping contour in the form of a V-shaped recess 40 which is complementary to the V-shaped protrusion 39. The barb 37*a* of the clamp arm 8*a* has a V-shaped recess 40 and the barb 37*b* has a V-shaped protrusion 39, each complementary to the corresponding barbs 37*c*, 37*d* of the other clamp arm 8*b*. To avoid unintended damages of blood vessels clamped between the clamp arms 8*a*, 8*b*, the corners of the V-shaped protrusions 39 and the corners of the V-shaped recesses 40 are rounded. Furthermore, rounded notches 41 are provided adjacent to the barbs 37*a*, 37*b*, 37*c*, 37*d*.

The distal end of the grasping section 38 of each clamp arm 8*a*, 8*b* is bent inwards towards the other clamp arms 8*a*, 8*b*. An engagement contour 42, in the present case a zigzag profile, is formed at the distal end of each clamp arm 8*a*, 8*b*. The engagement contours 42 of the clamp arms 8*a*, 8*b* are complementary to each other so that they engage with each other when the clamp arms 8*a*, 8*b* are closed.

Once the clamp device 3 has been set, the clamp arms 8*a*, 8*b* are to be locked in their closed state. For this purpose, the control wire 4 is pulled in the proximal direction, so that the pivot pin 9 engaging into the sliding grooves 16 passes the locking noses 17, thereby deforming elastically. When the pivot pin 9 has passed the locking noses 17, it cannot pass again in the distal direction due to the surface 19 extending perpendicular to the longitudinal direction X. In this way, it is prevented, that the clamp arms 8*a*, 8*b* can be opened unintentionally again.

As the next step, the clamp arms 8*a*, 8*b* are to be disconnected from the control wire 4. For this purpose, the control wire 4 is pulled further in proximal direction so that the holding arms 20*a*, 20*b* reach the enlarged proximal section 23 of the clamp housing 6. Due to their elastic restoring force, they spread apart, thus releasing the pivot pin 9 out of the recesses 21 formed in the holding arms 20*a*, 20*b*.

In order to uncouple/release the clamp housing 6 from the sheath device 2, the control wire 4 is further pulled back in proximal direction. Accordingly, the intermediate tube 36 is pressed between the coupling head 11 of the control wire 4 and the connecting element 30, thus pushing the connecting element 30 in the proximal direction. In this way, the engagement portions 34 formed at the connecting arms 33 come out of engagement from the ring groove 29 of the connect tube 26 and the through-apertures 28 of the clamp housing 6, so that the clamp housing 6 is released from the connect tube 26 of the sheath device 2.

Figure 27:
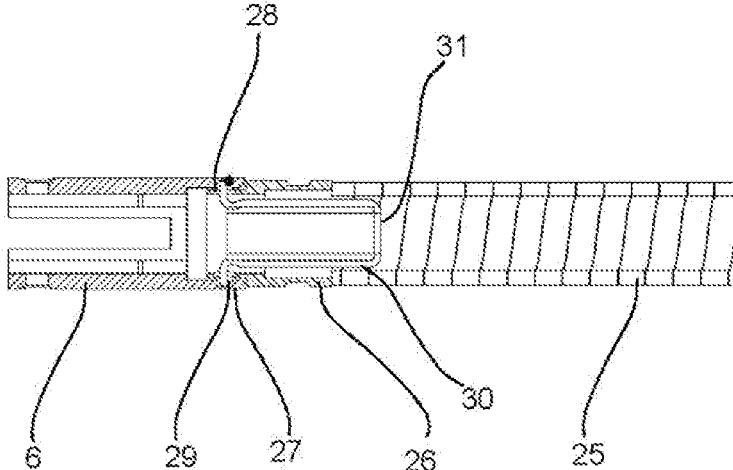
FIG. 27 a partial cross-sectional view of the distal end of a medical device according to a second embodiment of the present disclosure showing the sheath device, the connecting element and the clamp base.
Figure 28:
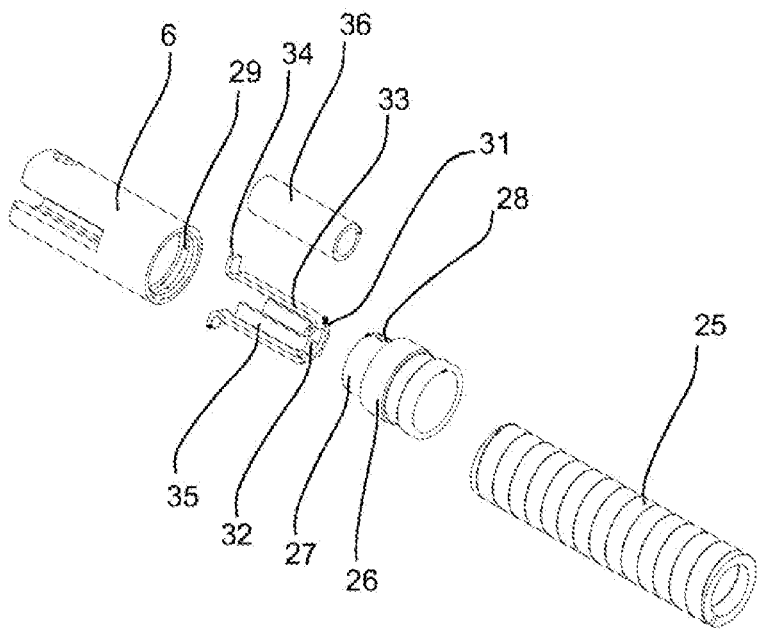
FIG. 28 a partial exploded view of the distal end of the medical device of FIG. 27.

FIGS. 27 and 28 show a second embodiment of a medical device according to the present disclosure.

This medical device is very similar to the one disclosed in FIGS. 1 to 26 and differs from this embodiment only in that the clamp housing 6 is not pushed into the connect tube 26 fixedly connected to the distal end of the sheath 25, but the clamp housing 6 forming an outer element is pushed onto the connect tube 26, thus forming an inner element. Accordingly, two through-apertures 28 arranged opposite each other are formed in the connect tube 26 and a ring groove 29 facing inwardly is formed in the clamp housing 6.

Consequently, the connecting element 30 formed practically identically to the one in the embodiment shown in FIGS. 1 to 26 engages with its engagement portions 34 of the connecting arms 33 through the through-apertures 28 of the connect tube 26 into the ring groove 29 of the clamp housing

6. In this way, the clamp housing 6 can be rotated relative to the sheath device by rotating the control wire 4.

Figure 29:
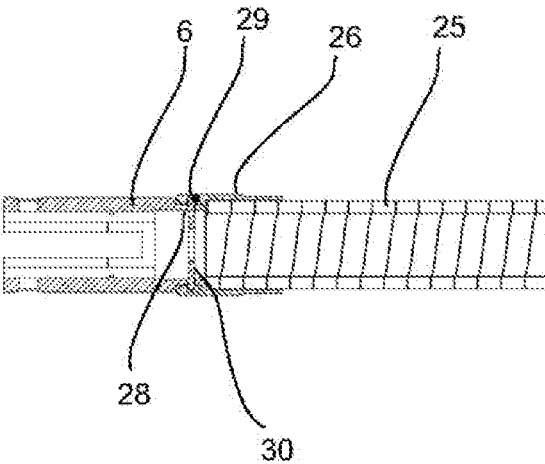
FIG. 29 a partial cross-sectional view of the distal end of a medical device according to a third embodiment of the present disclosure showing the sheath device, the connecting element and the clamp base.
Figure 30:
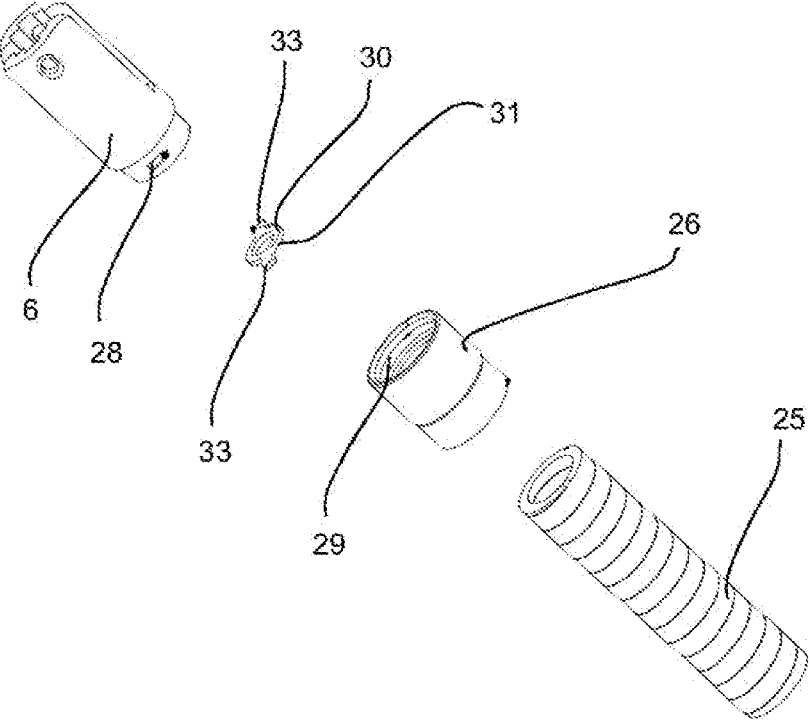
FIG. 30 a partial exploded view of the distal end of the medical device of FIG. 29.

FIGS. 29 and 30 show a third embodiment of the medical device according to the present disclosure. This medical device is very similar to the one disclosed in FIGS. 1 to 26, but the connecting element 30 differs from the one of the medical device of FIGS. 1 to 26. Presently, the connecting element 30 is formed as a planar disc having a central opening 32 and exactly two connecting arms 33 protruding radially outwardly. As it can be seen in FIG. 29, the connecting arms 33 are arranged in one plane with the disc and engage through the through-apertures 29 formed in the clamp housing 6 into the ring groove 29 formed in the connect tube 26.

In order to release the clamp housing 6 from the connect tube 26, the connecting element 30 is pushed by the coupling head 11 of the control wire 4 in the proximal direction, thus deforming the connecting element 30 and bringing the connecting arms 33 out of engagement from the ring groove 29.

Figure 31:
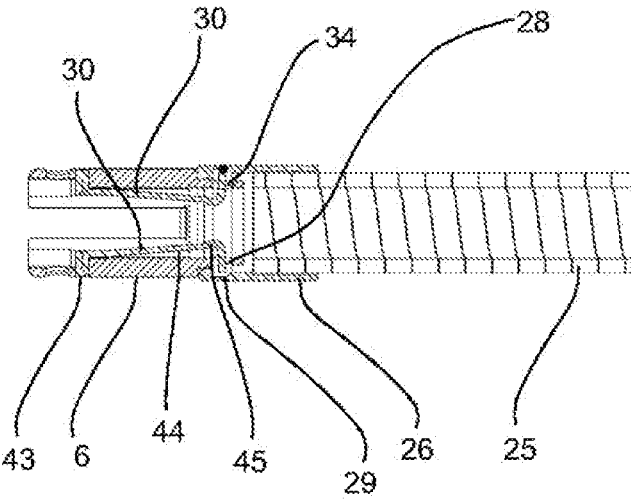
FIG. 31 a partial cross-sectional view of the distal end of a medical device according to a fourth embodiment of the present disclosure showing the sheath device, the connecting element and the clamp base.
Figure 32:
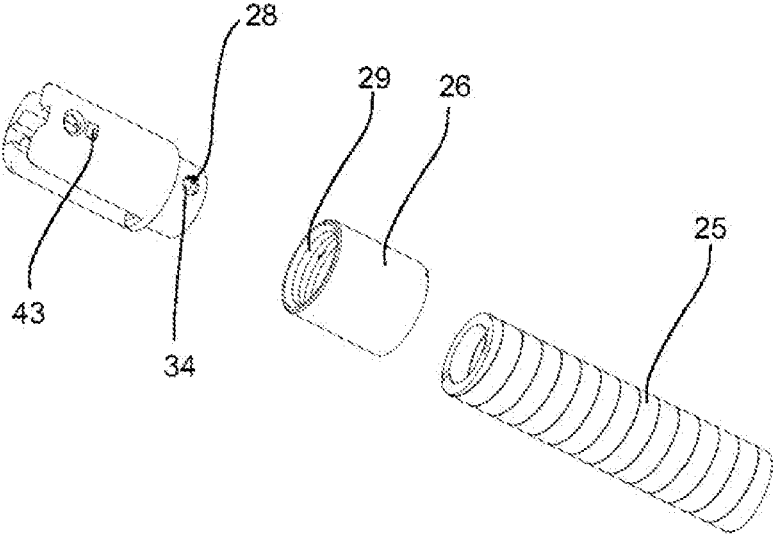
FIG. 32 a partial exploded view of the distal end of the medical device of FIG. 31.

FIGS. 31 and 32 show a further embodiment of the medical device according to the present disclosure.

This medical device is nearly identical to the one previously discussed. However, the sheath device 2 is connected to the clamp housing 6 by means of two connecting elements 30 in the form of elastic connecting arms that are positioned on opposite sides of the clamp housing 6. Specifically, the distal ends of the connecting elements 30 are fixedly attached to the clamp housing 6, whereas the free proximal ends of the connecting elements 30 form engagement portions 34 that engage corresponding engagement means provided in the inner circumferential surface of the connect tube 26 in order to couple the clamp housing 6 to the sheath device 2. Here, the clamp housing 6 is connected to the sheath device 2 by a push-in connection, wherein the proximal end of the clamp housing 6 is inserted/extends into the distal end of the connect tube 26. In the overlapping sections of the connect tube 26, through apertures 28 arranged opposite each other are formed in the clamp housing and a corresponding ring groove 29 is formed in the connect tube 26. The engagement portions 34 of the connecting elements 30 are pressed outwardly through the through-apertures 28 of the clamp housing 6 into the ring groove 29 of connect tube 26 in order to connect the clamp housing 6 to the sheath device 2.

The connecting elements 30 have inwardly bulged sections. Further, the distal ends of the connecting elements 30 are directed radially outwardly and extend into corresponding holding apertures 43 provided in the clamp housing 6 and are preferably fixed therein by welding, presently by a spot welding. The connecting elements 30 further have a straight section 44 following the distal end of the connecting elements 30, which is slanted inwardly with regard to the central longitudinal axis of the clamp housing, wherein the slanting angle is 5°. Between the straight section 44 and the engagement portions 34 of the connecting elements 30 an inwardly bulged section 45 is provided at the proximal end of the connecting elements 30.

A release arrangement for disconnecting the clamp housing 6 from the connect tube 26 is provided. This release arrangement comprises a protrusion 46 formed by the coupling head 11 provided at the distal end of the control wire 4. The protrusion 46 cooperates with and is located between the inwardly bulged sections 45 of the connecting elements 30 to press the inwardly bulged sections 45 outwardly elastically deforming the connecting elements 30 in such a way that their free ends are pressed. When the control wire

4 is pulled proximally and the protrusion 46 comes out of engagement of the connecting elements 30, the bulged sections 45 are redeformed inwardly by their elastic restoring force to obtain their original shape and the engagement portions 34 come out of engagement from the ring groove 29 formed in the connect tube 26.

The invention claimed is:

1. A medical device for causing hemostasis of blood vessel comprising:
   a handle;
   a sheath device, which is attached to the handle;
   a clamp device comprising a clamp housing defining a longitudinal direction with a clamp base in particular in the form of a sleeve provided on the distal end of the sheath device and at least two, in particular exactly two clamp arms, said clamp housing defining an interior space;
   a control wire extending through the sheath device and reversibly movable in the distal and proximal direction; and
   an actuator coupled to the proximal end of the control wire and actuable to reversibly move the control wire in the distal and proximal direction;
   wherein the clamp arms are each coupled to the distal end of the control wire and wherein the clamp device is actuable to open and close the clamp arms by a movement of the control wire such that a movement of the control wire in a proximal direction is translated into a closing movement of the clamp arms and a movement of the control wire in the distal direction is translated into an opening movement of the clamp arms;
   wherein the clamp arms are coupled to the distal end of the control wire via a pivot pin extending through corresponding through-holes provided in the proximal end sections of the clamp arms and being held releasably at the distal end of the control wire,
   where the pivot pin protrudes laterally on both sides from the clamp arms and the distal end of the control wire and
   two locking noses are provided on the clamp housing extending into the interior space of the clamp housing, wherein the locking noses are designed in such a way that they allow the pivot pin to pass them in the proximal direction but prevent passing of the pivot pin in the distal direction in order to lock the clamp arms in a closed state,
   wherein the clamp housing has on its inner surface two sliding grooves extending in the longitudinal direction and arranged opposite each other in such a way that each end section of the pivot pin engages into one sliding groove; and
   wherein the locking noses project from the ground of the respective sliding groove into the sliding groove.

2. The medical device according to claim 1, wherein each locking nose has on its distal side an inclined surface with respect to the longitudinal direction of the clamp housing and on its proximal side a surface extending perpendicular to the longitudinal direction.

3. The medical device according to claim 2, wherein the inclination angle of the inclined surface is at minimum 30° and/or at maximum 60°, preferably 45° with respect to the longitudinal direction of the clamp housing.

4. The medical device according to claim 1, wherein the pivot pin is of tubular shape.

5. The medical device according to claim 1, wherein the sliding grooves have a rectangular cross-section.

6. The medical device according to claim 1, wherein the locking noses extend over the entire width of the respective sliding groove.

7. The medical device according to claim 1, wherein the clamp housing comprises a central passage opening and two bearing arms extending in the distal direction from the clamp base, so that the interior space of the clamp housing is defined by the central passage opening and the space between the bearing arms.

8. The medical device according to claim 1, wherein a disengaging arrangement is provided which allows disconnecting the clamp arms from the control wire when the clamp arms are locked in the closed state and the control wire is further pulled in the proximal direction.

9. The medical device according to claim 8, wherein
   the control wire comprises a coupling head at its distal end,
   the coupling head comprising at least one pair of holding arms, which holding arms are moveable between a fixing position, in which the holding arms encompass the pivot pin, thus holding the pivot pin in particular in a form-fit manner, and a disengaging position, in which the holding arms are spread apart from each other, thus releasing the pivot pin,
   wherein the holding arms are biased towards their disengaging position, and
   the inner contour of the clamp housing cooperates with the holding arms in such a way that the holding arms are pressed towards each other into their fixing position as long as the holding arms extend into a distal section of the clamp housing, and that the holding arms return automatically into their disengaging position, when the control wire is pulled in the proximal direction such that the holding arms reach a proximal section of the clamp housing.

10. The medical device according to claim 9, wherein the inner contour of the clamp housing comprises one retaining groove assigned to each pair of holding arms, wherein the retaining groove receives the holding arms between its side walls such that the holding arms abut against the side walls and are held in their fixing position as long as the holding arms extend into the retaining groove,
    and each retaining groove leads proximally into an enlarged proximal section of the clamp housing having an enlarged opening size compared to the retaining groove so that the holding arms return automatically into their disengaging position, when the control wire is pulled in the proximal direction such that the holding arms reach the enlarged proximal section having an enlarged opening size compared to the width of the retaining groove.

11. The medical device according to claim 10, wherein the coupling head comprises exactly two pairs of holding arms which are arranged on laterally opposite sides of the clamp arms, and in that one retaining groove is arranged on both sides of the clamp arms.

12. The medical device according to claim 10, wherein the transition between the enlarged proximal section and the retaining groove is formed as a step.

13. The medical device according to claim 12, wherein the step is arranged with respect to the locking noses in such a way that the pivot pin passes the locking noses before the holding arms of the coupling head reach the enlarged proximal section and return into their disengaging position.

14. The medical device according to claim 10, wherein the sliding grooves are arranged in the retaining grooves, in particular in the grounds of the retaining grooves.

15. The medical device according to claim 9, wherein recesses for receiving the pivot pin are formed in the surfaces of the holding arms facing towards each other, wherein the recesses preferably extend over the entire thickness of the respective holding arm and/or preferably have an at least substantially semicircular cross-section.

16. The medical device according to claim 9, wherein the holdings arms of each pair are formed in a one-piece design so that the holding arms are elastically deformable between their fixing position and their disengaging position.

17. The medical device according to claim 1, wherein the clamp arms are provided as separate elements, which are coupled to the distal end of the control wire in a pivotal manner around a common pivot axis defined by the pivot pin.

\* \* \* \* \*